United States Patent
Van Dyke et al.

(10) Patent No.: US 12,011,198 B2
(45) Date of Patent: Jun. 18, 2024

(54) HUMERAL NAIL

(71) Applicant: Biomet Manufacturing, LLC, Warsaw, IN (US)

(72) Inventors: Scott Van Dyke, Warsaw, IN (US); Nikolaos Kanakaris, Leeds (GB); Brian Mullis, Zionsville, IN (US); Frank A Liporace, Englewood Cliffs, NJ (US); George J Haidukewych, Orlando, FL (US); Kiyoto Kinugasa, Kouchi (JP); Hisayoshi Inoue, Miyagi (JP)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/136,700

(22) Filed: Apr. 22, 2016

(65) Prior Publication Data
US 2016/0310176 A1 Oct. 27, 2016

Related U.S. Application Data

(60) Provisional application No. 62/152,339, filed on Apr. 24, 2015.

(51) Int. Cl.
*A61B 17/72* (2006.01)
*A61B 17/68* (2006.01)

(52) U.S. Cl.
CPC ............ *A61B 17/725* (2013.01); *A61B 17/72* (2013.01); *A61B 2017/681* (2013.01); *A61B 17/7233* (2013.01)

(58) Field of Classification Search
CPC . A61B 17/72; A61B 17/7291; A61B 17/7233; A61B 17/7241; A61B 17/7225; A61B 17/1725; A61B 17/7283

(Continued)

(56) References Cited

U.S. PATENT DOCUMENTS 5,472,444 A * 12/1995 Huebner ............... A61B 17/72
606/62
5,480,402 A * 1/1996 Kim .................. A61B 17/1725
606/64

(Continued)

FOREIGN PATENT DOCUMENTS

CA 2983664 C 9/2023
CN 102639074 A 8/2012

(Continued)

OTHER PUBLICATIONS

"European Application Serial No. 16720299.3, Communication Pursuant to Article 94(3) EPC mailed Nov. 28, 2019", 5 pgs.

(Continued)

*Primary Examiner* — Eduardo C Robert
*Assistant Examiner* — Tara Rose E Carter
(74) *Attorney, Agent, or Firm* — SCHWEGMAN LUNDBERG & WOESSNER, P.A.

(57) ABSTRACT

A humeral nail can include a nail longitudinal axis extending from a proximal portion to a distal portion, a first proximal through bore defining a first screw trajectory, a second proximal through bore defining a second screw trajectory, a third proximal through bore defining a third screw trajectory, a descending through bore defining a descending screw trajectory, and a calcar through bore defining a calcar screw trajectory. The first, second and third screw trajectories extend transverse to the nail longitudinal axis, the descending screw trajectory extends anterior to posterior and proximal to distal, and the calcar screw trajectory extends distal to proximal, anterior to posterior, and lateral to medial. In some examples, the calcar through bore defines at least two calcar screw trajectories.

20 Claims, 8 Drawing Sheets

(58) Field of Classification Search
USPC .................................................. 606/62–68
See application file for complete search history.

(56) References Cited

U.S. PATENT DOCUMENTS

| | | | | |
|---|---|---|---|---|
| 5,549,610 | A * | 8/1996 | Russell | A61B 17/72 606/62 |
| 6,296,645 | B1 * | 10/2001 | Hover | A61B 17/72 606/62 |
| 7,608,075 | B2 | 10/2009 | Tornier | |
| 7,655,009 | B2 | 2/2010 | Grusin | |
| 7,914,532 | B2 | 3/2011 | Shaver et al. | |
| 8,876,822 | B2 | 11/2014 | Fagan | |
| 2004/0172026 | A1 * | 9/2004 | Ekholm | A61B 17/72 606/62 |
| 2006/0122600 | A1 | 6/2006 | Cole | |
| 2006/0200142 | A1 | 9/2006 | Sohngen et al. | |
| 2007/0123873 | A1 | 5/2007 | Czartoski et al. | |
| 2007/0123878 | A1 * | 5/2007 | Shaver | A61B 17/72 606/64 |
| 2007/0255283 | A1 | 11/2007 | Ekholm et al. | |
| 2009/0157078 | A1 | 6/2009 | Mikol | |
| 2011/0046625 | A1 * | 2/2011 | Boileau | A61B 17/72 606/64 |
| 2012/0143192 | A1 * | 6/2012 | Watanabe | A61B 17/7233 606/64 |
| 2012/0197255 | A1 * | 8/2012 | Elghazaly | A61B 17/921 606/64 |
| 2012/0209268 | A1 | 8/2012 | Overes | |
| 2013/0116693 | A1 * | 5/2013 | Nelson | A61B 17/1725 606/64 |
| 2013/0274747 | A1 | 10/2013 | Fagan et al. | |
| 2014/0276828 | A1 * | 9/2014 | Howling | A61B 17/1725 606/64 |
| 2014/0316410 | A1 | 10/2014 | Overes | |

FOREIGN PATENT DOCUMENTS

| | | |
|---|---|---|
| CN | 103796602 A | 5/2014 |
| CN | 204033457 U | 12/2014 |
| CN | 204072294 U | 1/2015 |
| CN | 108124424 A | 6/2018 |
| DE | 20213166 U1 | 1/2004 |
| EP | 3884892 B1 | 9/2023 |
| JP | 2002253566 A | 9/2002 |
| JP | 2004081860 A | 3/2004 |
| JP | 2007125388 A | 5/2007 |
| JP | 2007275573 A | 10/2007 |
| JP | 2009512522 A | 3/2009 |
| JP | 2011511650 A | 4/2011 |
| JP | 2011519658 A | 7/2011 |
| JP | 2014531232 A | 11/2014 |
| JP | 2022080896 A | 5/2022 |
| WO | WO-2011002903 A2 | 1/2011 |
| WO | WO-2013037387 A1 | 3/2013 |
| WO | WO-2016172594 A1 | 10/2016 |

OTHER PUBLICATIONS

"Japanese Application Serial No. 2018-506806, Final Notification of Reasons for Refusal mailed Sep. 15, 2020", with English translation, 13 pages.
"Australian Application Serial No. 2016252884, First Examination Report mailed Apr. 20, 2020", 4 pgs.
"Chinese Application Serial No. 201680032929.X, Office Action mailed Mar. 30, 2020", w/ English Translation, 20 pgs.
"Chinese Application Serial No. 201680032929.X, Response filed Aug. 14, 2020 to Office Action mailed Mar. 30, 2020", w/ English claims, 11 pgs.
"European Application Serial No. 16720299.3, Response filed Apr. 8, 2020 to Communication Pursuant to Article 94(3) EPC mailed Nov. 28, 2019", 15 pgs.
"Japanese Application Serial No. 2018-506806, Office Action mailed Feb. 25, 2020", w/ English translation, 8 pgs.
"Japanese Application Serial No. 2018-506806, Response filed Aug. 25, 2020 to Office Action mailed Feb. 25, 2020", w/ English claims, 11 pgs.
"Australian Application Serial No. 2016252884, Response filed Mar. 30, 2021 to First Examination Report mailed Apr. 20, 2020", 14 pgs.
"Chinese Application Serial No. 201680032929.X, Office Action mailed Nov. 20, 2020", (W/ English Translation), 12 pgs.
"Chinese Application Serial No. 201680032929.X, Response filed Feb. 3, 2021 to Office Action mailed Nov. 20, 2020", (W/ English Translation of Claims), 9 pgs.
"Japanese Application Serial No. 2018-506806, Office Action mailed Mar. 2, 2021", (W/ English Translation), 6 pgs.
"Canadian Application Serial No. 2,983,664, Examiner's Rule 86(2) Requisition mailed Apr. 15, 2022", 3 pgs.
"Canadian Application Serial No. 2,983,664, Office Action mailed Jan. 16, 2023", 3 pgs.
"Canadian Application Serial No. 2,983,664, Response filed Nov. 8, 2022 to Examiner's Rule 86(2) Requisition mailed Jul. 15, 2022", 12 pgs.
"European Application Serial No. 21174513.8, Extended European Search Report mailed Nov. 5, 2021", 10 pgs.
"European Application Serial No. 21174513.8, Partial European Search Report mailed Aug. 18, 2021", 11 pgs.
"European Application Serial No. 21174513.8, Response filed Jun. 2, 2022 to Extended European Search Report mailed Nov. 5, 2021", 18 pgs.
"EXPERT TN Tibial Nail Surgical Technique", DePuy Synthes, www.depuysynthes.com, (Jun. 2022), 84 pgs.
"Japanese Application Serial No. 2018-506806, Examiners Decision of Final Refusal mailed Oct. 5, 2021", w/ English translation, 6 pgs.
"Japanese Application Serial No. 2018-506806, Notification of Reasons for Refusal mailed Apr. 11, 2023", w/ English Translation, 10 pgs.
"Japanese Application Serial No. 2018-506806, Notification of Reasons for Refusal mailed Oct. 31, 2023", w/ English Translation, 5 pgs.
"Japanese Application Serial No. 2018-506806, Notification of Reasons for Refusal mailed Nov. 15, 2022", w/ English Translation, 12 pgs.
"Japanese Application Serial No. 2018-506806, Preliminary Examination Report mailed Sep. 6, 2022", w/ English Translation, 2 pgs.
"Japanese Application Serial No. 2018-506806, Response filed Feb. 8, 2022 to Examiners Decision of Final Refusal mailed Oct. 5, 2021", w/ English claims, 19 pgs.
"Japanese Application Serial No. 2018-506806, Response filed Feb. 15, 2023 to Notification of Reasons for Refusal mailed Nov. 15, 2022", w/ English claims, 13 pgs.
"Japanese Application Serial No. 2018-506806, Response filed Jul. 11, 2023 to Notification of Reasons for Refusal mailed Apr. 11, 2023", w/ English claims, 12 pgs.
"Japanese Application Serial No. 2018-506806, Response filed Nov. 1, 2022 to Preliminary Examination Report mailed Sep. 6, 2022", w/ English claims, 11 pgs.
"Japanese Application Serial No. 2022-017290, Examiners Decision of Final Refusal mailed Jul. 18, 2023", W/English Translation, 17 pgs.
"Japanese Application Serial No. 2022-017290, Notification of Reasons for Rejection mailed Mar. 28, 2023", W/English Translation, 15 pgs.
"Japanese Application Serial No. 2022-017290, Response filed Jun. 28, 2023 to Notification of Reasons for Rejection mailed Mar. 28, 2023", w/ English claims, 15 pgs.
Hessmann, Martin H, et al., "Trauma, Upper Extremity", [online], AO foundation TK system Innovations, Feb. 2011), 6 pgs.
Tadashi, "Short femoral nail (1)", MB Orthopaedics, vol. 27, No. 8, (2014), 43-55.
"International Application Serial No. PCT/US2016/028998, International Preliminary Report on Patentability mailed Nov. 2, 2017", 9 pgs.

(56) References Cited

OTHER PUBLICATIONS

"Application Serial No. PCT/US2016/028998, Invitation to Pay Add'l Fees and Partial Search Report mailed Jun. 30, 2016", 7 pgs.
"International Application Serial No. PCT/US2016/028998, International Search Report mailed Aug. 26, 2016", 6 pgs.
"International Application Serial No. PCT/US2016/028998, Written Opinion mailed Aug. 26, 2016", 7 pgs.

* cited by examiner

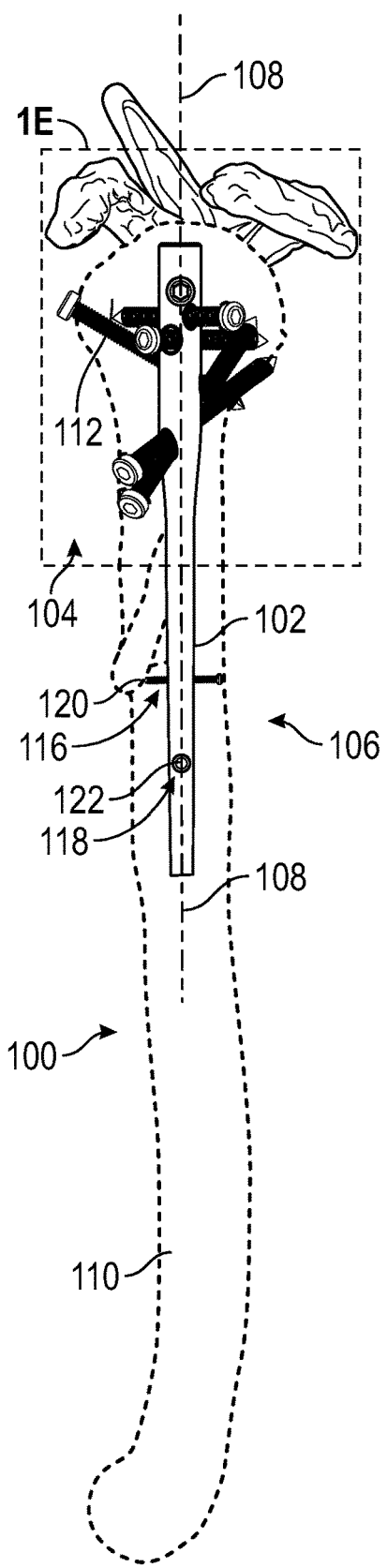
FIG. 1D
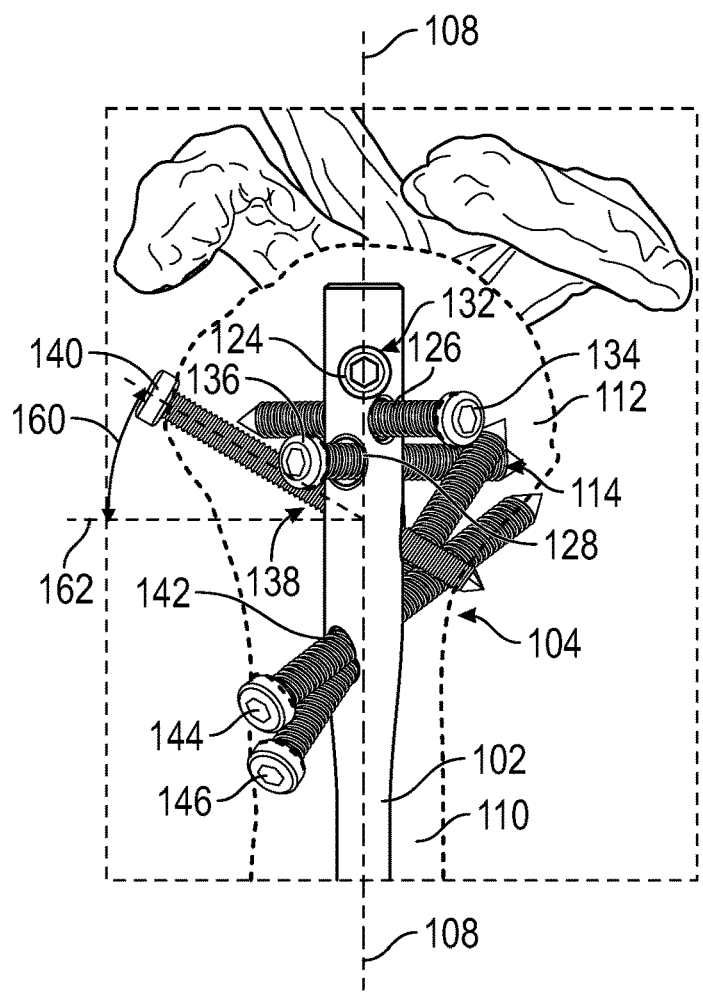
FIG. 1E
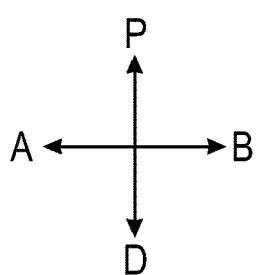

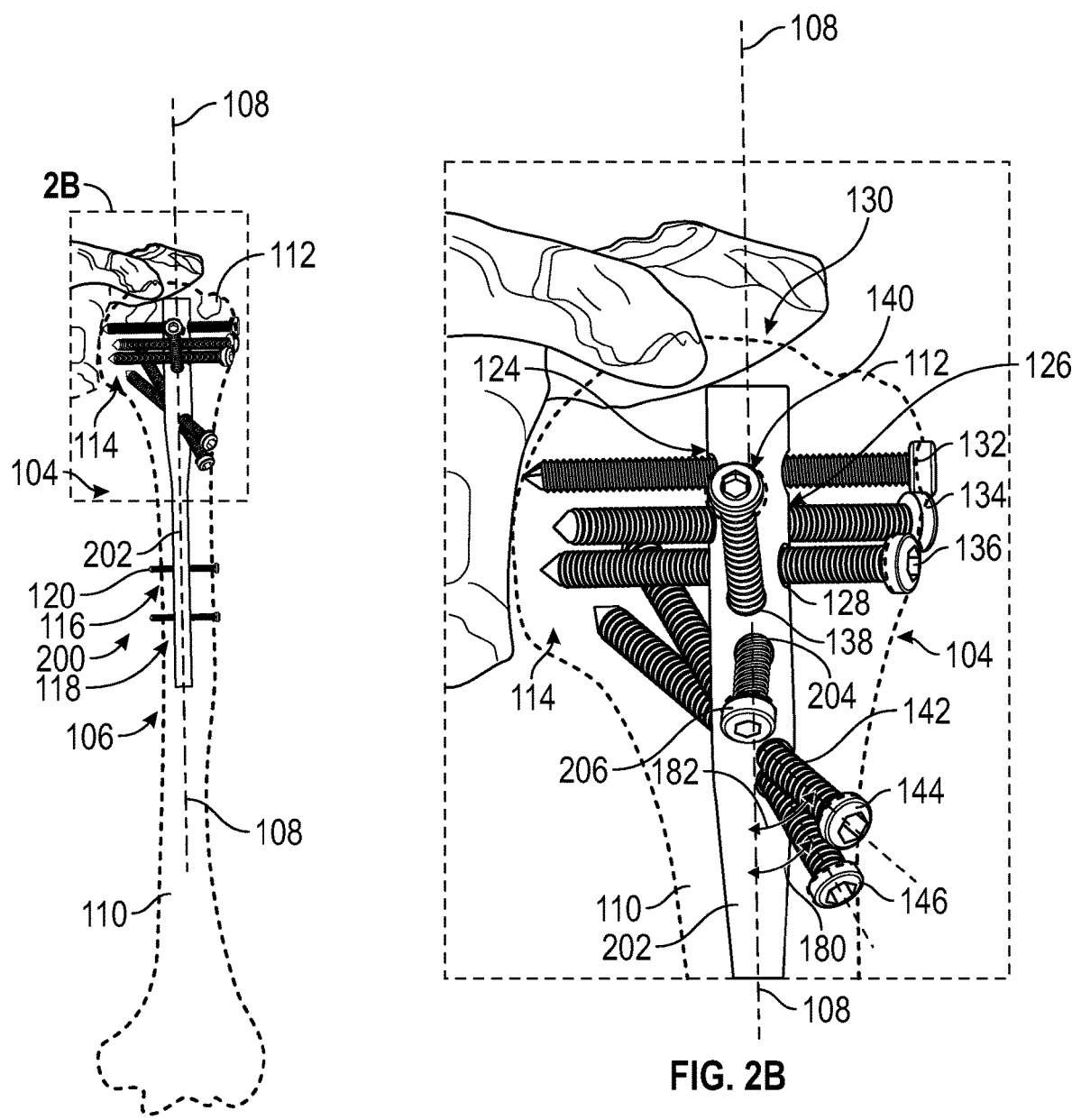
FIG. 2A
FIG. 2B
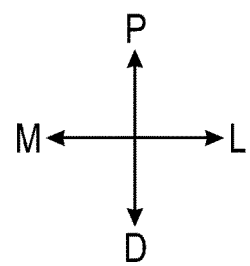

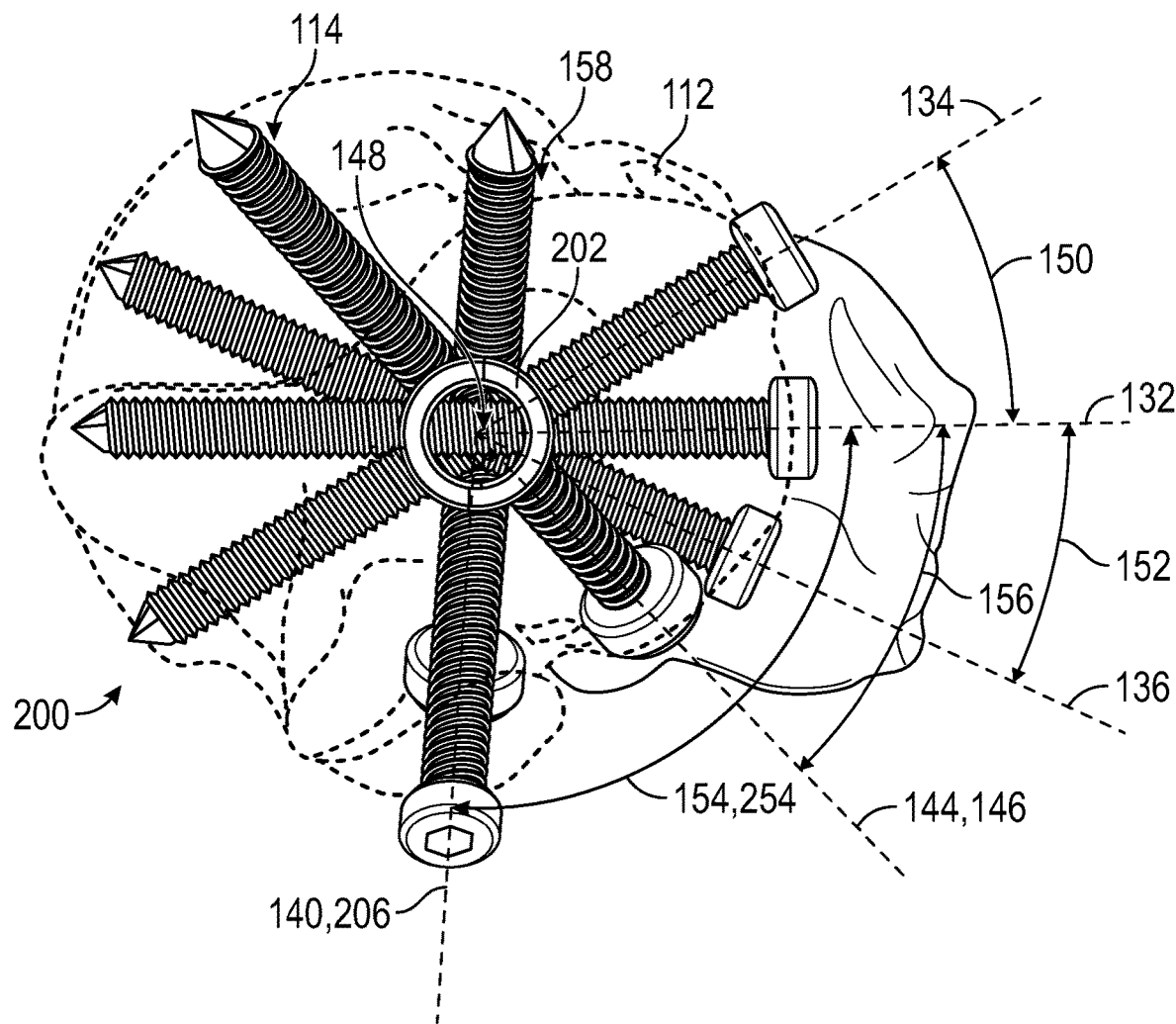
FIG. 2C
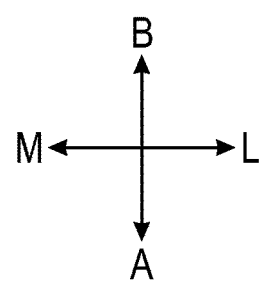

HUMERAL NAIL

CROSS-REFERENCE TO RELATED APPLICATIONS

This application claims the benefit of U.S. Provisional Application No. 62/152,339, filed on Apr. 24, 2015, the entire disclosure of which is incorporated herein by reference.

BACKGROUND

When using a humeral nail to treat fractures of the humerus, it is important to be able to effectively target certain anatomical landmarks in the vicinity of the humeral head while also avoiding vital vasculature and nerves. A specific anatomical target may differ in location from patient to patient due to differences in size and shape between each patient's anatomy. Some conventional humeral nails cannot effectively target the anatomical landmarks of a patient.

OVERVIEW

To better illustrate the instrument disclosed herein, a non-limiting list of examples is provided here:

In Example 1, a humeral nail can be provided that includes a nail body defining a nail longitudinal axis extending from a proximal portion to a distal portion of the nail body, and a descending through bore formed in the nail body and having a bore entrance positioned anterior and proximal relative to a bore exit and defining an anterior to posterior descending screw trajectory through the nail body.

In Example 2, the humeral nail of Example 1 is optionally configured such that the descending through bore is configured to receive a bone screw to target a patient's lesser tuberosity.

In Example 3, the humeral nail of Example 1 or Example 2 is optionally configured such that the descending through bore extends through the proximal portion of the humeral nail.

In Example 4, the humeral nail of any of Examples 1-3, optionally further includes an ascending through bore defining an ascending screw trajectory through the nail body that intersects the descending screw trajectory.

In Example 5, the humeral nail of Example 4 is optionally configured such that the ascending screw trajectory and the descending screw trajectory define an angle therebetween of at least 40 degrees in a proximal-distal direction.

In Example 6, a humeral nail includes a nail body defining a nail longitudinal axis extending from a proximal portion of the nail body to a distal portion of the nail body, a first proximal through bore formed in the nail body and defining a first screw trajectory extending transverse to the nail longitudinal axis, a second proximal through bore formed in the nail body and defining a second screw trajectory extending transverse to the nail longitudinal axis, a third proximal through bore formed in the nail body and defining a third screw trajectory extending transverse to the nail longitudinal axis, a descending through bore formed in the nail body and defining a descending screw trajectory extending anterior to posterior and proximal to distal, and a calcar through bore formed in the nail body and defining a calcar screw trajectory extending anterior to posterior, lateral to medial, and distal to proximal.

In Example 7, the humeral nail of Example 6 is optionally configured such that the first, second, and third proximal through bores, the descending through bore, and the calcar through bore extend through the proximal portion of the nail body.

In Example 8, the humeral nail of Example 6 or Example 7 is optionally configured such that the first proximal through bore defines the first screw trajectory as extending lateral to medial along a medial-lateral axis.

In Example 9, the humeral nail of any of Examples 6-8 is optionally configured such that the second proximal through bore defines the second screw trajectory as extending lateral to medial and posterior to anterior.

In Example 10, the humeral nail of any of Examples 6-9 is optionally configured such that the third proximal through bore defines the third screw trajectory as extending lateral to medial and anterior to posterior.

In Example 11, the humeral nail of any of Examples 6-10 is optionally configured such that the calcar through bore defines a variable angle calcar screw trajectory.

In Example 12, the humeral nail of any of Examples 6-11, optionally further includes an ascending through bore formed in the nail body and defining an ascending screw trajectory extending anterior to posterior and distal to proximal.

In Example 13, a humeral nail includes a humeral nail body defining a nail longitudinal axis extending from a proximal portion to a distal portion of the humeral nail body, and a calcar through bore extending through the humeral nail body and having a bore entrance positioned anterior and lateral relative to a bore exit, the calcar through bore defining at least two different calcar screw trajectories extending distal to proximal.

In Example 14, the humeral nail of Example 13 is optionally configured such that the bore entrance includes two intersecting ellipses.

In Example 15, the humeral nail of Example 13 or Example 14 is optionally configured such that the at least two different calcar screw trajectories differ in a proximal-distal direction and a medial-lateral direction.

In Example 16, the humeral nail of any of Examples 13-15 is optionally configured such that the bore entrance includes an opening in the shape of a figure eight.

In Example 17, the humeral nail of any of Examples 13-16 is optionally configured such that the calcar through bore defines at least three different calcar screw trajectories.

In Example 18, the humeral nail of any of Examples 13-17 is optionally configured such that the bore entrance includes three intersecting ellipses.

In Example 19, the humeral nail of any of Examples 13-18 is optionally configured such that each of the different calcar screw trajectories extend at an angle of 40 degrees to 60 degrees from the nail longitudinal axis.

In Example 20, the humeral nail of any of Examples 13-19 is optionally configured such that the bore entrance is positioned about 50 degrees anterior to a medial-lateral axis, and the bore exit is positioned about 50 degrees posterior to the medial-lateral axis.

In Example 21, the apparatus, system, or method of any one or any combination of Examples 1-20 can optionally be configured such that all elements or options recited are available to use or select from.

These and other examples and features of the present devices, systems, and methods will be set forth in part in the following Detailed Description. This overview is intended to provide a summary of subject matter of the present patent application. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 1D is a lateral to medial view of the humeral nail of FIGS. 1A-1C, in accordance with at least one example of the present disclosure.

FIG. 1E is a magnified view of the proximal portion of the humeral nail of FIG. 1D, in accordance with at least one example of the present disclosure.

FIG. 2A is an anterior to posterior view of a humeral nail, in accordance with at least one example of the present disclosure.

FIG. 2B is a magnified view of a proximal portion of the humeral nail of FIG. 2A, in accordance with at least one example of the present disclosure.

FIG. 2C is a top view of the humeral nail of FIGS. 2A and 2B, in accordance with at least one example of the present disclosure.

DETAILED DESCRIPTION

A humeral nail can include a nail body defining a nail longitudinal axis extending from a proximal portion to a distal portion. In some examples, the proximal portion of the humeral nail can include a plurality of through bores formed through the nail body; for example, a plurality of proximal through bores, a descending through bore and a calcar through bore. In some examples, the descending through bore can define a descending screw trajectory extending anterior to posterior and proximal to distal. In some examples, the humeral nail can further include an ascending through bore defining an ascending screw trajectory that intersects the descending screw trajectory. In some examples, the calcar through bore can define a variable angle calcar screw trajectory.

In at least one example, the humeral nail can provide screw trajectories for targeting anatomical landmarks in the vicinity of the humeral head while also avoiding vital vasculature and nerves. Further, providing these screw trajectories through the humeral nail can provide stable locking, which can be especially important if a screw is driven into poor bone stock. In at least one example, the humeral nail can provide screw trajectories that allow patient-specific anatomical landmarks to be targeted.

In some examples, the descending screw trajectory can target the lesser tuberosity of a patient. In at least one example, the descending screw trajectory can more effectively target the lesser tuberosity than conventional anterior to posterior screw trajectories which extend transverse to the nail longitudinal axis, and can sometimes be too low for certain patients to capture the lesser tuberosity.

In some examples, the variable angle calcar screw trajectory can target the calcar region of the humeral head. In at least one example, the variable angle calcar screw trajectory can more effectively target a patient-specific calcar region than conventional fixed-trajectory systems.

Further areas of applicability will become apparent from the description provided herein. The description and specific examples in this summary are intended for purposes of illustration only and are not intended to limit the scope of the present disclosure. The term "transverse to" as used herein, is generally interchangeable with "normal to" or "perpendicular to." The terms proximal, distal, medial, lateral, anterior, and posterior describe the humeral nail with reference to its orientation when implanted in a patient's humerus. FIGS. 1A-2F include an indication of the orientation of the axes, in which "P" indicates the proximal axis, "D" indicates the distal axis, "M" indicates the medial axis, "L" indicates the lateral axis, "A" indicates the anterior axis, and "B" indicates the posterior axis.

Figures 1A, 1B:
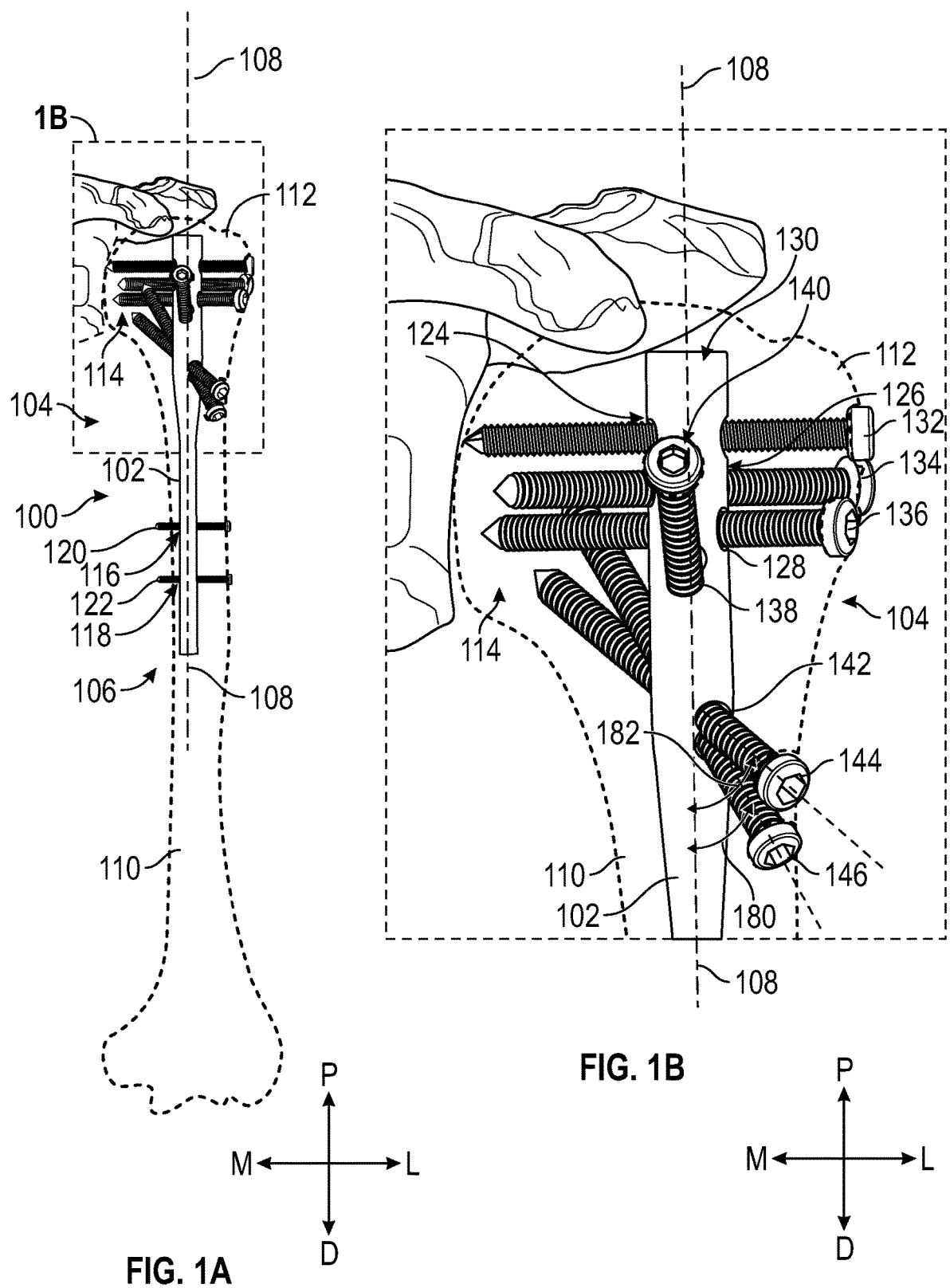
FIG. 1A is an anterior to posterior view of a humeral nail, in accordance with at least one example of the present disclosure.
FIG. 1B is a magnified view of a proximal portion of the humeral nail of FIG. 1A, in accordance with at least one example of the present disclosure.

FIG. 1A is an anterior to posterior view of a humeral nail 100, in accordance with at least one example of the present disclosure. The humeral nail 100 can include a humeral nail body 102 having a proximal end 104 and a distal end 106, and defining a nail longitudinal axis 108 extending along the length of the humeral nail body 102 from the proximal end 104 to the distal end 106. In the illustrated example, the humeral nail body 102 is depicted implanted within a patient's humerus 110, which generally includes a humeral head 112 and a calcar region 114.

In some examples, the humeral nail body 102 can include one or more distal through bores 116, 118 formed in the humeral nail body 102 and extending through the distal portion 106, each distal through bore 116, 118 defining a distal screw trajectory 120, 122. In at least one example, the one or more distal through bores 116, 118 can define distal screw trajectories 120, 122 extending transverse to the nail longitudinal axis 108. In some examples, each of the one or more distal through bores 116, 118 can define a distal screw trajectory 120, 122 extending at any angle, in any direction, through the distal portion 106 of the humeral nail body 102. While the illustrated example depicts two distal through bores 116, 118, in other examples the humeral nail body 102 can include no distal through bores, a single distal through bore, or more than two distal through bores.

FIG. 1B is a magnified view of the proximal portion 104 of the humeral nail 100 of FIG. 1A, in accordance with at least one example of the present disclosure. In at least one example, the humeral nail body 102 can include a first proximal through bore 124, a second proximal through bore 126, and a third proximal through bore 128, each of the proximal through bores 124, 126, 128 extending through the proximal portion 104, each through bore formed in the humeral nail body 102.

In at least one example, the first proximal through bore 124 can be the first most proximal through bore of the humeral nail body 102. In some examples, the first proximal through bore 124 can be positioned at a distance of between approximately 10 millimeters and approximately 15 millimeters distal of a proximal end 130 of the humeral nail body 102. In at least one example, the first proximal through bore 124 can be positioned at a distance of approximately 12.5 millimeters distal of the proximal end 130 of the humeral nail body 102. In some examples, the first proximal through bore 124 can define a first screw trajectory 132 extending through the proximal portion 104. In at least one example, the first screw trajectory 132 can extend transverse to the nail longitudinal axis 108. In at least one example, the first screw trajectory 132 can extend lateral to medial along the medial-lateral axis.

In at least one example, the second proximal through bore 126 can be the second most proximal through bore of the humeral nail body 102. In some examples, the second proximal through bore 126 can be positioned at a distance of between approximately 17 millimeters and approximately 21 millimeters distal of the proximal end 130 of the humeral nail body 102. In at least one example, the second proximal through bore 126 can be positioned at a distance of approximately 19 millimeters from the proximal end 130 of the humeral nail body 102. In some examples, the second proximal through bore 126 can define a second screw trajectory 134 extending through the proximal portion 104. In at least one example, the second screw trajectory 134 can extend transverse to the nail longitudinal axis 108. In at least one example, the second screw trajectory 134 can extend lateral to medial and posterior to anterior.

In at least one example, the third proximal through bore 128 can be the third most proximal through bore of the humeral nail body 102. In some examples, the third proximal through bore 128 can be positioned at a distance of between approximately 23 millimeters and approximately 28 millimeters distal of the proximal end 130 of the humeral nail body 102. In at least one example, the third proximal through bore 128 can be positioned at a distance of approximately 25.5 millimeters from the proximal end 130 of the humeral nail body 102. In some examples, the third proximal through bore 128 can define a third screw trajectory 136 extending through the proximal portion 104. In at least one example the third screw trajectory 136 can extend transverse to the nail longitudinal axis 108. In at least one example, the third screw trajectory 136 can extend lateral to medial and anterior to posterior.

In other examples, the humeral nail body 102 can include more proximal through bores, less proximal through bores, and each proximal through bore can be at any position and in any orientation.

In some examples, the humeral nail body 102 can include a descending through bore 138 extending through the proximal portion 104. In at least one example, the descending through bore 138 can be the fourth most proximal through bore of the humeral nail body 102. In some examples, the descending through bore 138 can be positioned at a distance of between approximately 30 millimeters and approximately 34 millimeters distal of the proximal end 130 of the humeral nail body 102. In at least one example, the descending through bore 138 can be positioned at a distance of approximately 32 millimeters distal of the proximal end 130 of the humeral nail body 102. In some examples, the descending through bore 138 can define a descending screw trajectory 140 extending through the proximal portion 104. In at least one example, the descending screw trajectory 140 can extend anterior to posterior and proximal to distal.

In some examples, the humeral nail body 102 can include a calcar through bore 142 extending through the proximal portion 104. In at least one example, the calcar through bore 142 can be the fifth most proximal through bore of the humeral nail body 102. In some examples, the calcar through bore 142 can be positioned at a distance of between approximately 45 millimeters and approximately 50 millimeters distal of the proximal end 130 of the humeral nail body 102. In at least one example, the calcar through bore 142 can be positioned at a distance of approximately 47.5 millimeters from the proximal end 130 of the humeral nail body 102.

In some examples, the calcar through bore 142 can define one or more calcar screw trajectories 144, 146 extending through the proximal portion 104. In some examples, each of the one or more calcar screw trajectories 144, 146 can comprise a variable angle trajectory. In some examples, the calcar through bore 142 can define at least two calcar screw trajectories 144, 146. In some examples, the calcar through bore 142 can define at least three calcar screw trajectories. In at least one example, the calcar screw trajectory 140 can extend anterior to posterior, lateral to medial, and distal to proximal. In at least one example, the calcar screw trajectories 140 can vary in angle 180, 182 relative to the nail longitudinal axis 108 or the proximal-distal axis. In at least one example, each of the calcar screw trajectories 144, 146 can extend at an angle of 40 degrees to 60 degrees from the nail longitudinal axis 108. In at least one example, the angle 180 of one calcar screw trajectory 146 can be 40 degrees from the nail longitudinal axis 108, and the angle 182 of another calcar screw trajectory 144 can be 60 degrees form the nail longitudinal axis 108. In some examples, the calcar through bore 142 can comprise an ellipse or other elongated opening, so as to provide a variable calcar screw trajectory 144, 146 that allows for a plurality of trajectories. In at least one example, the calcar through bore 142 can allow for a screw to be placed at any angle between 40 degrees and 60 degrees.

Figure 1C:
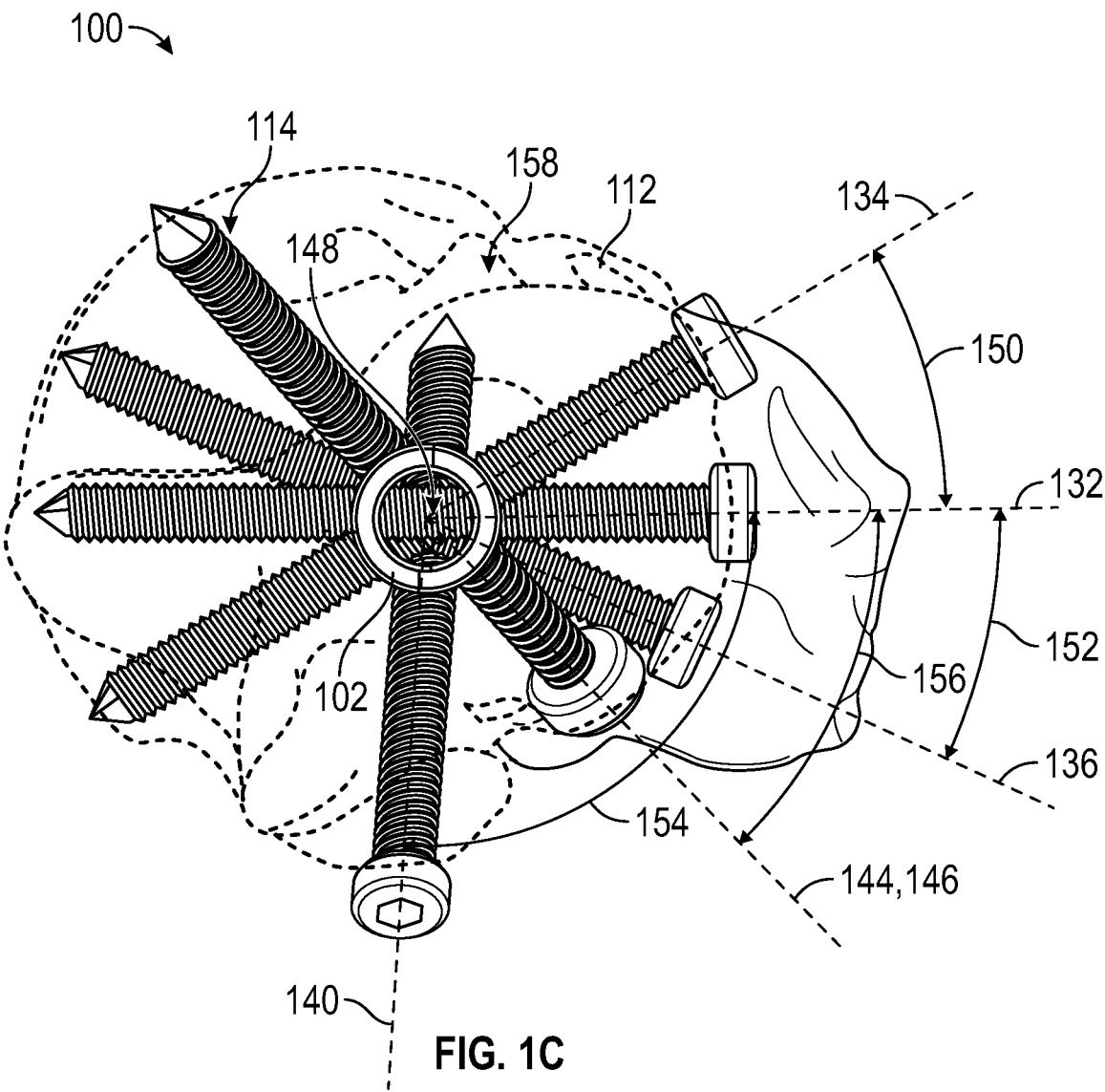
FIG. 1C is a top view of the humeral nail of FIGS. 1A and 1B, in accordance with at least one example of the present disclosure.

FIG. 1C is a top view of the humeral nail 100 of FIGS. 1A and 1B, in accordance with at least one example of the present disclosure. In the illustrated example, the humeral nail body 102 can form a lumen 148. In at least one example, the lumen 148 can extend along the nail longitudinal axis 108 for the length of the humeral nail body 102.

As can be seen in the illustrated example, the first screw trajectory 132 can extend lateral to medial approximately along the medial-lateral axis. In some examples, the second screw trajectory 134 can extend lateral to medial and posterior to anterior. In at least one example, the second screw trajectory 134 can extend at an angle 150 posterior to the medial-lateral axis. In at least one example, the angle 150 of the second screw trajectory 134 can be approximately 30 degrees posterior to the medial-lateral axis. In at least one example, the second screw trajectory 134 can extend at a coronal angle of between approximately 25 and 35 degrees posterior to the medial-lateral plane.

In some examples, the third screw trajectory 136 can extend lateral to medial and anterior to posterior. In at least one example, the third screw trajectory 136 can extend at an angle 152 anterior to the medial-lateral axis. In at least one example, the angle 152 of the third screw trajectory 136 can be approximately 25 degrees anterior to the medial-lateral axis. In at least one example, the third screw trajectory 136 can extend at a coronal angle of between approximately 20 and 30 degrees anterior to the medial-lateral plane.

In some examples, the descending screw trajectory 140 can extend proximal to distal and anterior to posterior. In at least one example, the descending screw trajectory 140 can extend proximal to distal, anterior to posterior, and medial to lateral. In at least one example the descending screw trajectory 140 can extend at an angle 154 anterior to the medial-lateral axis. In at least one example, the angle 154 of the descending screw trajectory 140 can be approximately 95 degrees anterior to the medial-lateral axis. In at least one example, descending screw trajectory 140 can extend in the anterior to posterior direction at an angle of between approximately 60 and 80 degrees from the nail longitudinal axis 108.

In some examples, one or more of the calcar screw trajectories 144, 146 can extend anterior to posterior, lateral to medial, and distal to proximal. In at least one example, one or more of the calcar screw trajectories 144, 146 can extend at an angle 156 anterior to the medial-lateral axis. In at least one example, the angle 156 of one or more of the calcar screw trajectories 144, 146 can be approximately 50 degrees anterior to the medial-lateral axis. In at least one example, one or more of the calcar screw trajectories 144, 146 extends in the anterior to posterior direction at an angle of between approximately 45 and 60 degrees from the nail longitudinal axis 108.

In at least one example, one or more of the calcar screw trajectories 144, 146 extends at a coronal angle of between approximately 45 and 55 degrees from the medial-lateral axis, and at an angle of between approximately 40 and 60 degrees from the nail longitudinal axis 108. In at least one example, the variable angle calcar screw trajectory can be located inside the nail body 102 at approximately 40 degrees, at approximately 50 degrees, and at approximately 60 degrees from the nail longitudinal axis 108. In at least one example. In at least one example, the variable angle calcar screw trajectory can be located inside the nail body 102 at approximately 40 degrees from the nail longitudinal axis 108 and at a coronal angle of approximately 35-40 degrees from the medial-lateral axis, at approximately 50 degrees from the nail longitudinal axis 108 and at a coronal angle of approximately 50 degrees from the medial-lateral axis, and at approximately 60 degrees from the nail longitudinal axis 108 and at a coronal angle of approximately 60-65 degrees from the medial-lateral axis.

In the illustrated example, the first proximal through bore 124, the second proximal through bore 126, and the third proximal through bore 128 are configured such that the respective first, second, and third screw trajectories, 132, 134, 136 target the humeral head 112. In the illustrated example, the descending through bore 138 is configured such that the descending screw trajectory 140 targets a lesser tuberosity 158. In the illustrated example, the calcar through bore 142 is configured such that one or more of the variable calcar screw trajectories 144, 146 target the calcar region 114.

As can be seen in the illustrated example, the trajectories 132, 134, 136, 140, 144, 146 are splayed from the top view to provide better support in the humeral head 112. In at least one example, the trajectories can be spread out from a top view (such as the top view of FIG. 1C) so as to target multiple anatomical landmarks.

FIG. 1D is a lateral to medial view of the humeral nail 100 of FIGS. 1A-1C, and FIG. 1E is a magnified view of the proximal portion 104 of the humeral nail 100 of FIG. 1D, in accordance with at least one example of the present disclosure. In the illustrated example, it is clear that one of the calcar screw trajectories 146 can better target the calcar than another calcar screw trajectory 144. As such, a practitioner can orient a bone screw to extend through the calcar through bore 142 such that it follows the selected calcar screw trajectory 146 to target the calcar region. In at least one example, the practitioner can select a selected calcar screw trajectory of a plurality of calcar screw trajectories to target patient-specific anatomical landmarks.

In some examples, the descending screw trajectory 140 can extend proximal to distal. In some examples, the descending screw trajectory 140 can extend at an angle 160 proximal to a medial-lateral axis 162. In at least one example, the angle 160 of the descending screw trajectory 140 can be approximately 30 degrees proximal to the medial-lateral axis 162.

Each of the bore holes 124, 126, 128, 138, 142 can include a bore entrance and a bore exit, which, in the illustrated example are indicated by the direction of the screws showing the screw trajectories, 132, 134, 136, 140, 144, 146. That is, the screw enters through the bore entrance of the through bore and extends through the bore exit of the through bore. In the illustrated examples, the head of each screw is on the bore entrance side of each through bore, and the tip of the screw is on the bore exit side of each through bore. The screw trajectories 132, 134, 136, 140, 144, 146 are generally described directionally as extending from the bore entrance to the bore exit of the respective borehole 124, 126, 128, 138, 142. For example, a screw trajectory extending anterior to posterior is generally illustrated with the head of the screw on the anterior side of the humeral nail body 102, and the tip of the screw on the posterior side of the humeral nail body 102.

FIG. 2A-2F are various views of a humeral nail 200 including a humeral nail body 202, in accordance with at least one example of the present disclosure. In some examples, the humeral nail body 202 of the humeral nail 200 can be generally the same as the humeral nail body 102 of the humeral nail 100 described with reference to FIGS. 1A-1E except the humeral nail body 202 can include an ascending through bore 204. In at least one example, the ascending through bore 204 can define an ascending screw trajectory 206.

In some examples, the ascending through bore 204 can define an ascending screw trajectory 206 extending anterior to posterior and distal to proximal. In at least one example, the ascending screw trajectory 206 can extend anterior to posterior, distal to proximal, and medial to lateral. In at least one example the ascending screw trajectory 206 can extend at an angle 254 anterior to the medial-lateral axis. In at least one example, the angle 254 of the ascending screw trajectory 206 can be approximately 95 degrees anterior to the medial-lateral axis. In the example illustrated in FIG. 2C, the angle 254 of the ascending screw trajectory 206 with respect to the medial-lateral axis can be equal to the angle 154 of the descending screw trajectory 140 with respect to the medial-later axis, such that the ascending screw trajectory 206 and the descending screw trajectory 140 align in a top view of the humeral nail 200.

As can be seen in the illustrated examples, the trajectories 132, 134, 136, 140, 144, 146, 206 are splayed about the nail longitudinal axis 108 to provide better support in the humeral head 112. In at least one example, the trajectories can be spread out from a top view (such as the top view of FIG. 2C) so as to target multiple anatomical landmarks.

In some examples, the ascending screw trajectory 206 can extend at an angle 208 distal to an anterior-posterior axis. In some examples, the ascending screw trajectory 206 can intersect the descending screw trajectory 140 within the humeral nail body 202 at an intersection point 218. In at least one example, the ascending screw trajectory 206 can intersect the descending screw trajectory 140 within the lumen 148 of the humeral nail body 202. In some examples, a screw can only be used in one of the ascending through bore 204 and the descending through bore 138 at any given time. As such, the ascending through bore 204 and the descending through bore 138 allow a practitioner to select a patient-specific screw trajectory 140, 206 based on the specific patient's anatomy. For example, the descending screw trajectory 206 can be selected to target the patient's lesser tuberosity or the ascending screw trajectory 140 can be selected to target the calcar area 114 of the humeral head 112.

In some examples, the descending screw trajectory 206 and the ascending screw trajectory 140 can define an angle 220 therebetween along the nail longitudinal axis 108 or in the proximal-distal direction. In some examples, the angle 220 can be the combination of the angle 106 and the angle 208. In at least one example, the angle 220 can be at least a minimum angle to maintain the structural integrity of the ascending and descending through bores 204, 138. In at least one example, the minimum angle 220 can be approximately 40 degrees. In some examples, each of the ascending screw trajectory 206 and the descending screw trajectory 140 can extend at any angle relative to the distal-proximal axis, as long as the angle 220 therebetween is at least 40 degrees. In at least one example, the angle 208 can be approximately 45 degrees. In at least one example, the angle 160 can be approximately 10 degrees. In some examples, the angle 208 can be approximately 45 degrees and the angle 160 can be approximately 15 degrees.

Figure 2D:
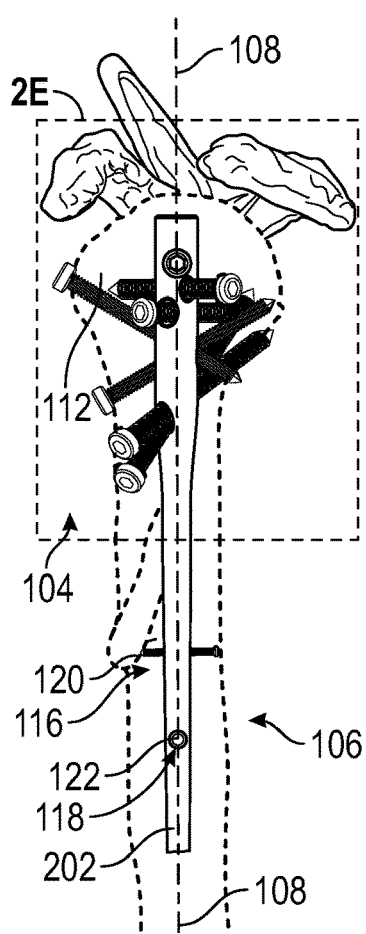
FIG. 2D is a lateral to medial view of the humeral nail of FIGS. 2A-2C, in accordance with at least one example of the present disclosure.
Figure 2E:
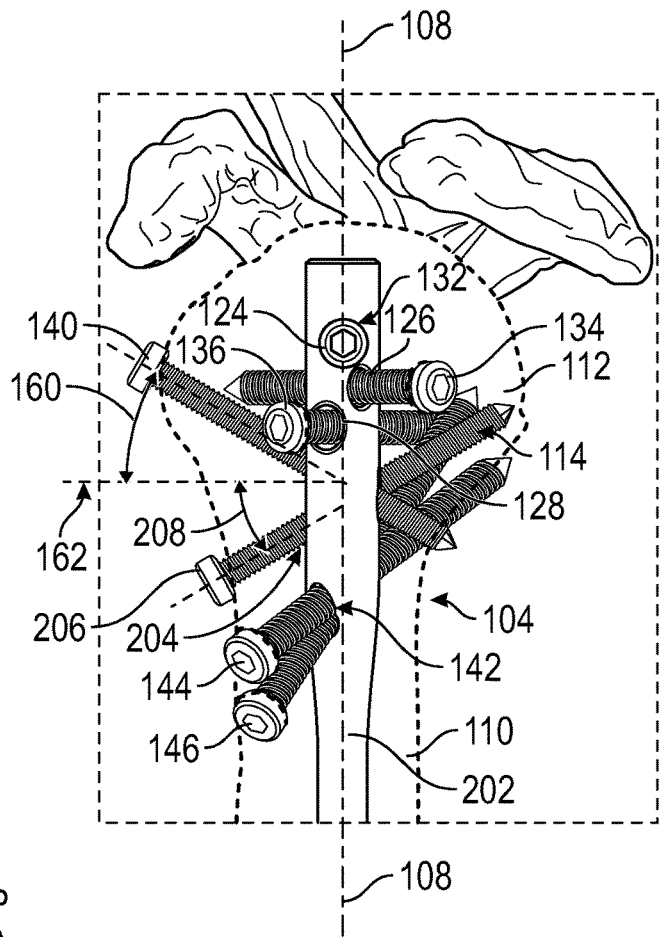
FIG. 2E is a magnified view of the proximal portion of the humeral nail of FIG. 2D, in accordance with at least one example of the present disclosure.
Figure 2F:
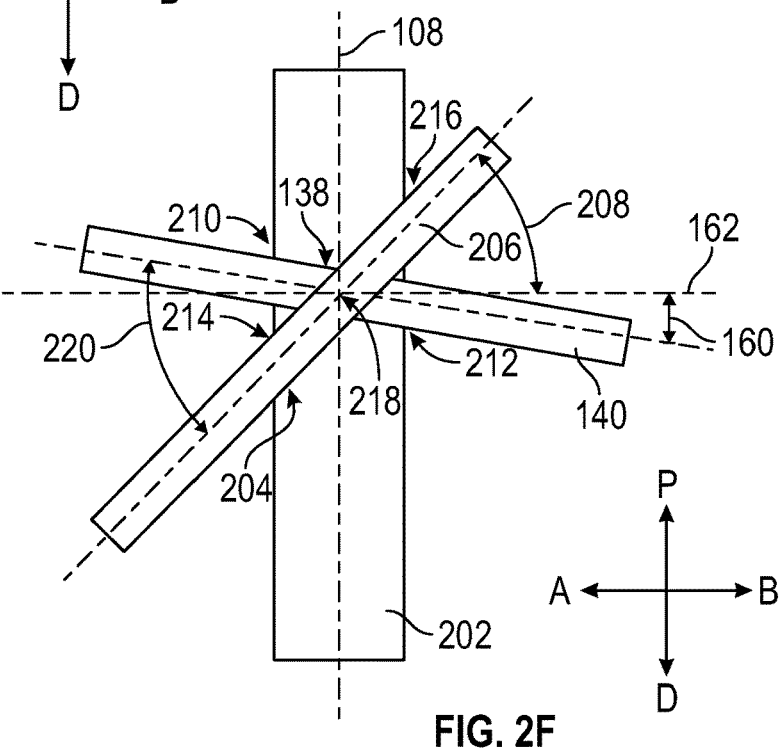
FIG. 2F is a block diagram of an ascending screw and a descending screw, in accordance with at least one example of the present disclosure.

In the illustrated example of FIG. 2F, the descending through bore 138 can include a bore entrance 210 and a bore exit 212. In some examples, the bore entrance 210 can be anterior and proximal relative to the bore exit 212. In at least one example, the bore entrance 210 can be proximal, medial, and anterior relative to the bore exit 212. In some examples, the bore entrance 210 and the bore exit 212 define the descending screw trajectory 140. In the illustrated example, the ascending through bore 204 can include a bore entrance 214 and a bore exit 216. In some examples, the bore entrance 214 can be anterior and distal relative to the bore exit 216. In at least one example, the bore entrance 214 can be distal, medial, and anterior to the bore exit 216. In some examples, the bore entrance 214 and the bore exit 216 define the ascending screw trajectory 206.

Each of the bore holes 124, 126, 128, 138, 142, 204 can include a bore entrance and a bore exit, which in the illustrated example are indicated by the direction of the screws showing the screw trajectories, 132, 134, 136, 140, 144, 146, 206. That is, the screw enters through the bore entrance of the through bore and extends through the bore exit of the through bore. In the illustrated examples, the head of each screw is on the bore entrance side of each through bore, and the tip of the screw is on the bore exit side of each through bore. The screw trajectories 132, 134, 136, 140, 144, 146, 206 are generally described directionally as extending from the bore entrance to the bore exit of the respective borehole 124, 126, 128, 138, 142, 204. For example, a screw trajectory extending anterior to posterior is generally illustrated with the head of the screw on the anterior side of the humeral nail body 102, 202, and the tip of the screw on the posterior side of the humeral nail body 102, 202.

Figure 3A:
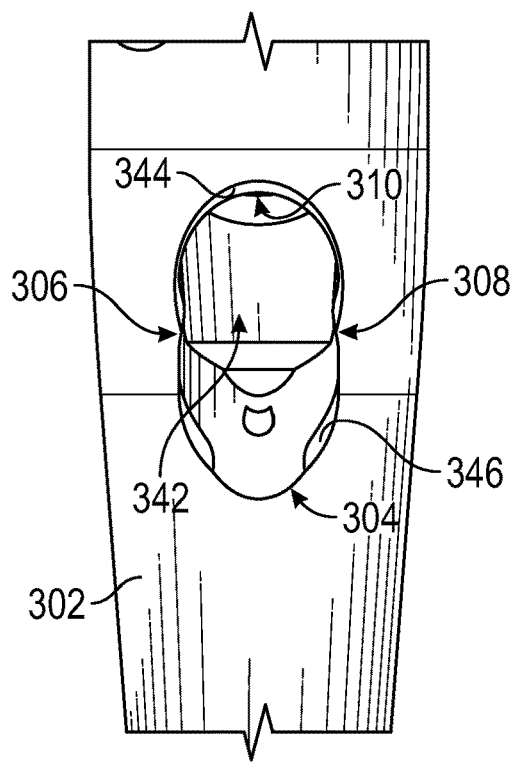
FIG. 3A is a perspective view of a bore entrance of a calcar through bore, in accordance with at least one example of the present disclosure.

FIG. 3A is a perspective view of a bore entrance 304 of a calcar through bore 342 formed in a humeral nail body 302, in accordance with at least one example of the present disclosure. As discussed above with reference to the calcar through bore 142, the calcar through bore 342 can define a variable angle screw trajectory. In the illustrated example, the calcar through bore 342 defines two different calcar screw trajectories corresponding to calcar screw trajectories 144, 146 (see FIGS. 1A-2E).

In some examples, the bore entrance 304 can include two intersecting ellipses 344, 346. In at least one example, the bore entrance 304 can include an opening approximately in the shape of a figure eight. In some examples, a first curved seat 344 (corresponding to the first calcar screw trajectory 144) can be positioned proximal to a second curved seat 346 (corresponding to the second calcar screw trajectory). In at least one example, the first curved seat 344 and the second curved seat 346 can meet at locking edges 306, 308. In some examples, the locking edges 306, 308 can be configured to retain a screw in either the first calcar screw trajectory 144 or the second calcar screw trajectory 146. In some examples, the curved seats 344, 346 can be sloped or tapered from the outside diameter of the humeral nail body 302 to the lumen 148. In at least one example, the slope or taper can provide a seating surface for the desired angle of the calcar screw trajectory.

Figure 3B:
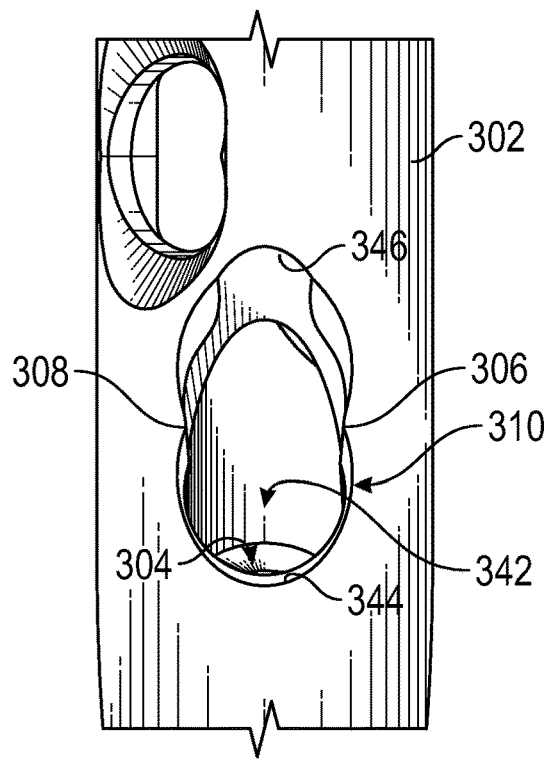
FIG. 3B is a perspective view of a bore exit of the calcar through bore of FIG. 3A, in accordance with at least one example of the present disclosure.

FIG. 3B is a perspective view of a bore exit 310 of the calcar through bore 342 of FIG. 3A, in accordance with at least one example of the present disclosure. In some examples, the bore entrance 304 can be positioned distal to the bore exit 310, such that the calcar screw trajectories 144, 146 extend distal to proximal. In some examples, the bore entrance 304 can be positioned anterior and lateral relative to the bore exit 310. In at least one example, the bore entrance 304 can be positioned 50 degrees anterior to the medial-lateral axis, and the bore exit 310 can be positioned about 50 degrees posterior to the medial-lateral axis.

In at least one example, this calcar screw trajectory establishes a screw in the medial-posterior quadrant of the humeral head and would provide more stability to the user than conventional calcar screw trajectories. This location on the anterior part of the nail also avoids major branches of the axillary nerve that conventional calcar screw trajectories would be in danger of hitting. At this location, the screw head avoids this region and the axillary nerve becomes smaller and less susceptible to damage.

In some examples, the bore exit 310 can include two intersecting ellipses 344, 346. In at least one example, the bore exit 310 can include an opening approximately in the shape of a figure eight. In some examples, a first curved seat 344 (corresponding to the first calcar screw trajectory 144) can be positioned distal to a second curved seat 346 (corresponding to the second calcar screw trajectory). In at least one example, the first curved seat 344 and the second curved seat 346 can meet at locking edges 306, 308. In some examples, the locking edges 306, 308 can be configured to retain a screw in either the first calcar screw trajectory 144 or the second calcar screw trajectory 146. In some examples, it is important that bone screws go through the humeral nail and are locked in position, especially if the screws are driven into poor bone stock. In at least one example, the calcar through bore 342 can define two calcar screw trajectories 144, 146 that vary relative to the proximal-distal axis. In some examples, the curved seats 344, 346 and the locking edges 306, 308 can differ in size, orientation and dimension from the bore entrance 304 to the bore exit 310.

In some examples, the curved seats 344, 346 can be sloped or tapered from the outside diameter of the humeral nail body 302 to the lumen 148. In at least one example, the slope or taper can provide a seating surface for the desired angle of the calcar screw trajectory. In the illustrated example, the first calcar screw trajectory 144 and the second calcar screw trajectory 146 intersect, such that the practitioner can only place one screw through the calcar through bore 342 at any given time. In some examples, the practitioner can select a patient-specific trajectory of the first and second calcar screw trajectories 144, 146 based on the patient's specific anatomy.

Figure 4A:
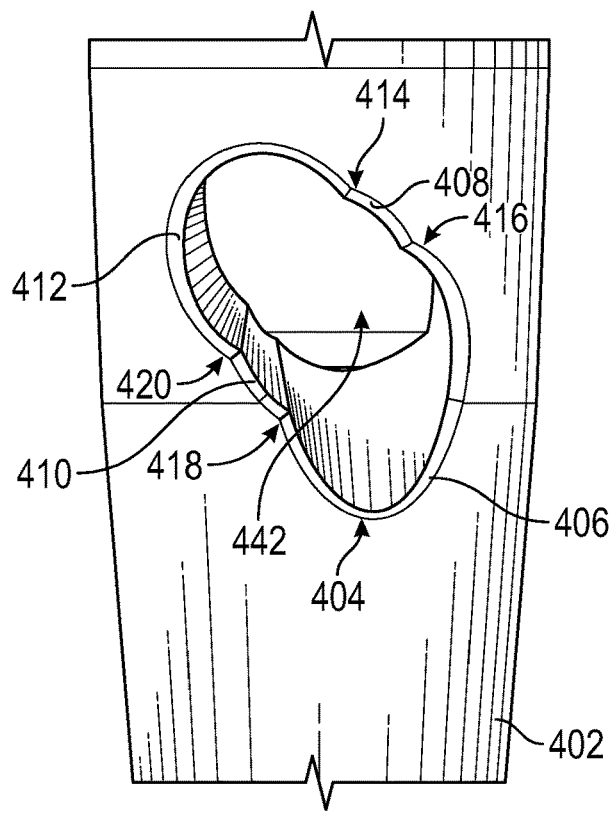
FIG. 4A is a perspective view of a bore entrance of a calcar through bore, in accordance with at least one example of the present disclosure.

FIG. 4A is a perspective view of a bore entrance 404 of a calcar through bore 442 formed in a humeral nail body 402, in accordance with at least one example of the present disclosure. As discussed above with reference to the calcar through bore 142, the calcar through bore 442 can define a variable angle screw trajectory. In the illustrated example, the calcar through bore 442 defines three different calcar screw trajectories.

In some examples, the bore entrance 404 can include four curved seats 406, 408, 410, 412, each curved seat configured to receive a screw along one of the three screw trajectories. In some examples, the bore entrance 404 can include three intersecting ellipses 406, 412 (curve seats 408, 410 combine to form one of the three intersecting ellipses). In at least one example, the first curved seat 406 can be positioned distal and lateral relative to the second curved seat 408, 410 and the third curved seat 412. In at least one example, the third curved seat 412 can be positioned proximal and medial relative to the first curved seat 406 and the second curved seat 408, 410. In at least one example, the curved seats 406, 408, 410, 412 can meet at locking edges 414, 416, 418, 420. In some examples, the locking edges 414, 416, 418, 420 can be configured to retain a screw in each of the first, second, and third calcar screw trajectories. In some examples, it is important that bone screws go through the humeral nail and are locked in position, especially if the screws are driven into poor bone stock.

In some examples, the curved seats 406, 408, 410, 412 can be sloped or tapered from the outside diameter of the humeral nail body 402 to the lumen 148. In at least one example, the slope or taper can provide a seating surface for the desired angle of the calcar screw trajectory. In at least one example, the calcar through bore 442 can include more than four curved surfaces 406, 408, 410, 412 and more than four locking edges 414, 416, 418, 420, such that the calcar through bore 442 can define more than three different calcar screw trajectories.

Figure 4B:
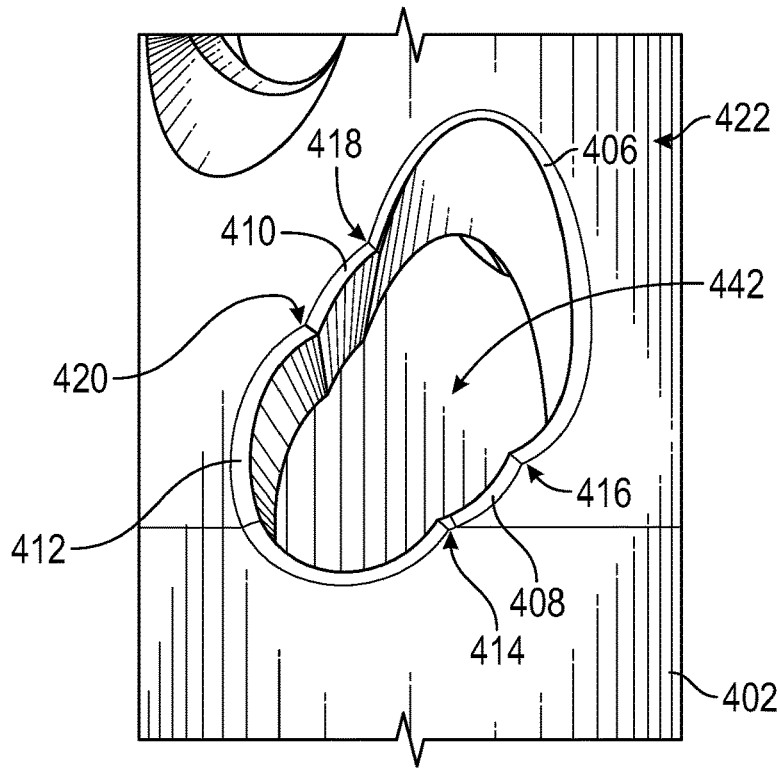
FIG. 4B is a perspective view of a bore exit of the calcar through bore of FIG. 4A, in accordance with at least one example of the present disclosure.

FIG. 4B is a perspective view of a bore exit 422 of the calcar through bore 402 of FIG. 4A, in accordance with at least one example of the present disclosure. In some examples, the bore entrance 404 can be positioned distal to the bore exit 422, such that the each of the calcar screw trajectories extend distal to proximal. In some examples, the bore entrance 404 can be positioned anterior and lateral relative to the bore exit 422. In at least one example, the bore entrance 404 can be positioned 50 degrees anterior to the medial-lateral axis, and the bore exit 422 can be positioned about 50 degrees posterior to the medial-lateral axis.

In some examples, the bore exit 422 can include four curved seats 406, 408, 410, 412, each curved seat configured to receive a screw along one of the three screw trajectories. In some examples, the bore exit 422 can include three intersecting ellipses 406, 412 (curve seats 408, 410 combine to form one of the three intersecting ellipses). In at least one example, the first curved seat 406 can be positioned proximal and medial relative to the second curved seat 408, 410 and the third curved seat 412. In at least one example, the third curved seat 412 can be positioned distal and lateral relative to the first curved seat 406 and the second curved seat 408, 410. In at least one example, the curved seats 406, 408, 410, 412 can meet at locking edges 414, 416, 418, 420. In some examples, the locking edges 414, 416, 418, 420 can be configured to retain a screw in each of the first, second, and third calcar screw trajectories. In some examples, it is important that bone screws go through the humeral nail and are locked in position, especially if the screws are driven into poor bone stock.

In some examples, the curved seats 406, 408, 410, 412 can be sloped or tapered from the outside diameter of the humeral nail body 402 to the lumen 148. In at least one example, the slope or taper can provide a seating surface for the desired angle of the calcar screw trajectory. In at least one example, the calcar through bore 442 can include more than four curved surfaces 406, 408, 410, 412 and more than four locking edges 414, 416, 418, 420, such that the calcar through bore 442 can define more than three different calcar screw trajectories. In the illustrated example, the first, second, and third calcar screw trajectories intersect, such that the practitioner can only place one screw through the calcar through bore 442 at any given time. In some examples, the practitioner can select a patient-specific trajectory of the first, second, and third calcar screw trajectories based on the patient's specific anatomy. In at least one example, the calcar through bore 442 can define at least three calcar screw trajectories that vary relative to the proximal-distal axis and the medial-lateral axis.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A humeral nail comprising:
a nail body defining a nail longitudinal axis extending from a proximal portion to a distal portion of the nail body;
a descending through bore formed in the proximal portion of the nail body a proximal end of the descending through bore positioned at a distance between 30 millimeters and 34 millimeters distally from a proximal end of the nail body and defining an anterior to posterior descending screw trajectory through the nail body descending at an angle of between 60 degrees and 80 degrees from the nail longitudinal axis, wherein the bore entrance is configured to be positioned anterior and proximal relative to the bore exit when the humeral nail is implanted in a humerus of a patient; and
a variable angle calcar through bore formed in the nail body and defining a calcar screw trajectory configured to target a calcar region of the patient, the calcar screw trajectory extending anterior to posterior, lateral to medial, and distal to proximal.

2. The humeral nail of claim 1, wherein the descending through bore is configured to receive a bone screw to target a patient's lesser tuberosity.

3. The humeral nail of claim 1, wherein the descending through bore extends through the proximal portion of the humeral nail.

4. The humeral nail of claim 1, further comprising:
an ascending through bore defining an ascending screw trajectory through the nail body that intersects the descending screw trajectory within a lumen of the nail body.

5. The humeral nail of claim 4, wherein the ascending screw trajectory and the descending screw trajectory define an angle therebetween of at least 40 degrees in a proximal-distal direction.

6. A humeral nail comprising:
a nail body defining a nail longitudinal axis extending from a proximal portion of the nail body to a distal portion of the nail body;
a first proximal through bore formed in the nail body and defining a first screw trajectory extending transverse to the nail longitudinal axis;
a second proximal through bore formed in the nail body and defining a second screw trajectory extending transverse to the nail longitudinal axis;
a third proximal through bore formed in the nail body and defining a third screw trajectory extending transverse to the nail longitudinal axis;
a descending through bore formed in the nail body and defining a descending screw trajectory configured to extend anterior to posterior and proximal to distal when the humeral nail is implanted in a humerus of a patient; and
a calcar through bore formed in the nail body and defining a calcar screw trajectory configured to target a calcar region of the patient, the calcar screw trajectory extending anterior to posterior, lateral to medial, and distal to proximal.

7. The humeral nail of claim 6, wherein the first, second, and third proximal through bores, the descending through bore, and the calcar through bore extend through the proximal portion of the nail body.

8. The humeral nail of claim 6, wherein the first proximal through bore defines the first screw trajectory as extending lateral to medial along a medial-lateral axis.

9. The humeral nail of claim 6, wherein the second proximal through bore defines the second screw trajectory as extending lateral to medial and posterior to anterior.

10. The humeral nail of claim 6, wherein the third proximal through bore defines the third screw trajectory as extending lateral to medial and anterior to posterior.

11. The humeral nail of claim 6, wherein the calcar through bore defines a variable angle calcar screw trajectory.

12. The humeral nail of claim 6, further comprising:
an ascending through bore formed in the nail body and defining an ascending screw trajectory extending anterior to posterior and distal to proximal.

13. A humeral nail comprising:
a humeral nail body defining a nail longitudinal axis extending from a proximal portion to a distal portion of the humeral nail body; and
a calcar through bore extending through the humeral nail body and defining at least two different calcar screw trajectories extending distal to proximal, wherein each of the at least two different calcar screw trajectories is configured to target a calcar region of a patient wherein a bore entrance of the calcar through bore is configured to be positioned anterior and lateral relative to a bore exit when the humeral nail is implanted in a humerus of the patient.

14. The humeral nail of claim 13, wherein the bore entrance comprises two intersecting ellipses.

15. The humeral nail of claim 13, wherein the at least two different calcar screw trajectories differ in a proximal-distal direction and a medial-lateral direction.

16. The humeral nail of claim 13, wherein the bore entrance comprises an opening in the shape of a figure eight.

17. The humeral nail of claim 13, wherein the calcar through bore defines at least three different calcar screw trajectories.

18. The humeral nail of claim 13, wherein the bore entrance comprises three intersecting ellipses.

19. The humeral nail of claim 13, wherein each of the different calcar screw trajectories extend at an angle of 40 degrees to 60 degrees from the nail longitudinal axis.

20. The humeral nail of claim 13, wherein the bore entrance is positioned 50 degrees anterior to a medial-lateral axis, and the bore exit is positioned 50 degrees posterior to the medial-lateral axis.

* * * * *